United States Patent [19]

Shiokawa et al.

[11] Patent Number: 4,812,454
[45] Date of Patent: Mar. 14, 1989

[54] NITROMETHYLENE DERIVATIVES AND THEIR USE AS INSECTICIDES

[75] Inventors: Kozo Shiokawa, Kanagawa; Shinichi Tsuboi, Tokyo; Shinzo Kagabu, Tokyo; Koichi Moriya, Tokyo, all of Japan; Bernd Baasner, Leverkusen, Fed. Rep. of Germany

[73] Assignee: Nihon Tokushu Noyaku Seizo K.K., Tokyo, Japan

[21] Appl. No.: 109,803

[22] Filed: Oct. 19, 1987

Related U.S. Application Data

[62] Division of Ser. No. 899,190, Aug. 22, 1986, Pat. No. 4,772,620.

[30] Foreign Application Priority Data

Aug. 27, 1985 [JP] Japan ................................ 60-186592

[51] Int. Cl.$^4$ ................ A61K 31/435; A61K 31/495; C07D 401/08
[52] U.S. Cl. ................................ 514/256; 514/218; 514/341; 540/553; 544/333; 546/276
[58] Field of Search ................ 544/333, 335; 514/256

[56] References Cited

FOREIGN PATENT DOCUMENTS 2514402 10/1976 Fed. Rep. of Germany ...... 546/278
2732660 10/1976 Fed. Rep. of Germany ...... 546/278

OTHER PUBLICATIONS

Thornber, Isosterism and Molecular Modifications in Drug Design, pp. 563–580 (1979).

Primary Examiner—Mary C. Lee
Assistant Examiner—J. Richter
Attorney, Agent, or Firm—Sprung Horn Kramer & Woods

[57] ABSTRACT

The present invention provides novel nitromethylene derivatives of the formula (I)

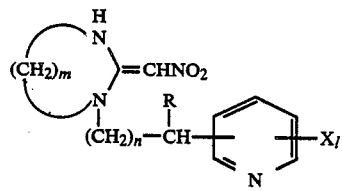

wherein R represents a hydrogen atom or an alkyl group, X represents a haloalkyl, haloalkoxy, haloalkylthio, haloalkylsulfinyl, haloalkylsulfonyl, nitro, cyano, thiocyanato, haloalkenyl, haloalkynyl, hydroxyl, alkoxycarbonyl, amino, acyl, dialkylamino, aclamino or alkoxy group, l represents 1, 2 or 3. provided that when l is 1, X does not represent an alkoxy group and when l is 2 or 3, not all substituents X represent an alkoxy group, m represent 2, 3 or 4, and n represents 0 or 1, and the use of the new compounds as insecticides.

8 Claims, No Drawings

NITROMETHYLENE DERIVATIVES AND THEIR USE AS INSECTICIDES

This is a division of application Ser. No. 899,190, filed Aug. 22, 1986, now U.S. Pat. No. 4,772,620.

The present invention relates to novel nitromethylene derivatives, to processes for their preparation and to their use as insecticides.

It has already been disclosed that a certain nitromethylene derivative has insecticidal activities. (see DE-OS No. 2,514,402)

There have now been found novel nitromethylene derivatives of the formula (I)

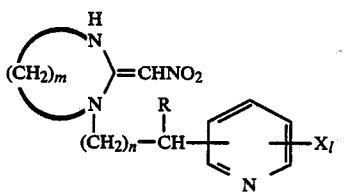

wherein R represents a hydrogen atom or an alkyl group, X represents a haloalkyl, haloalkoxy, haloalkylthio, haloalkylsulfinyl, haloalkylsulfonyl, nitro, cyano, thiocyanato, haloalkenyl, haloalkynyl, hydroxyl, alkoxycarbonyl, amino, acyl, dialkylamino, acylamino or alkoxy group, l represents 1, 2 or 3 provided that when l is 1, X does not represent an alkoxy group and when l is 2 or 3, not all substituents X represent an alkoxy group, m represents 2, 3 or 4, n represents 0 or 1.

The compounds of the formula (I) are obtained when (a) the compounds of the formula (II)

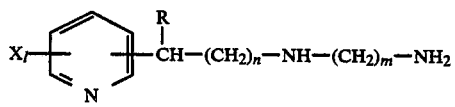

wherein R, X, l, m and n are as defined above, are reacted with the compounds of the formula (III)

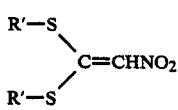

wherein R' represents a lower alkyl group or a benzyl group, or the two R' groups together may represent a lower alkylene group having at least 2 carbon atoms and may form a ring together with the sulfur atoms adjacent thereto, in the presence of inert solvents, or (b) the compounds of the formula (IV)

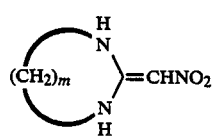

wherein m is as defined above, are reacted with the compounds of the formula (V)

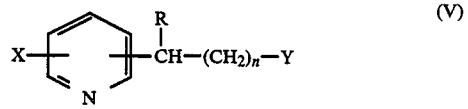

wherein R, X, l, and n are as defined above, Y represents a halogen atom or a group of the formula —O-SO$_2$R" in which R" represents a lower alkyl group or an aryl group, in the presence of inert solvents, if appropriate, in the presence of bases.

The novel nitromethylene derivatives exhibit powerful insecticidal properties.

Surprisingly, the nitromethylene derivatives according to the invention exhibit a substantially greater and much more excellent insecticidal action than the closest known compounds from the afore mentioned prior art.

In addition, the nitromethylene derivatives according to the invention also exhibit a remarkable insecticidal action against harmful insects, in particular sucking insects typified by insects of Hemiptera such as aphids, plant hoppers and leaf hoppers, which have aquired resistance to organic phosphate and carbamate type-insecticides caused by having long been used.

Among the compounds of the formula (I), according to the invention, preferred compounds are those in which R is a hydrogen atom or an alkyl group having 1 to 4 carbon atoms, X is a C$_1$-C$_4$alkyl group substituted by fluoro, chloro and/or bromo, a C$_1$-C$_4$ alkoxy group substituted by fluoro and/or chloro, a C$_1$-C$_4$ alkylthio group substituted by fluoro and/or chloro, a C$_1$-C$_4$ alkylsulfinyl group substituted by fluoro and/or chloro, a C$_1$-C$_4$ alkylsulfonyl group substituted by fluoro and/or chloro, a nitro group, a cyano group, a thiocyanato group, a C$_2$-C$_3$ alkenyl group substituted by fluoro and/or chloro, a C$_2$-C$_3$ alkylnyl group substituted by fluoro and/or chloro, a hydroxyl group, an alkoxycarbonyl group having C$_1$-C$_2$ alkyl, an amino group, an acetyl group, a dialkylamino group having C$_1$-C$_2$ alkyl, an acetamide group or a methoxy group, l is 1 or 2 provided that when l is 1, X does not represent a methoxy group and when l is 2, not all substituents X represent a methoxy group, m is 2 or 3, and n is 0.

Very particularly preferred compounds of the formula (I) are those in which R is a hydrogen atom or a methyl group, X is a C$_1$-C$_2$ fluoro-substituted alkyl group, a C$_1$-C$_2$ fluoro-substituted alkoxy group, a C$_1$-C$_2$ fluoro-substituted alkylthio group, a C$_1$-C$_2$ fluoro-substituted alkylsulfinyl group, a C$_1$-C$_2$ fluoro-substituted alkylsulfonyl group, a nitro group, a cyano group, a thiocyanato group, a chloro-substituted vinyl group, a fluoro-substituted propargyl group, a hydroxy group, a methoxycarbonyl group, an amino group, an acetyl group, a dimethylamino group or an acetamide group, l is 1 or 2, m is 2 or 3, and n is 0.

Specifically, the following compounds may be mentioned:

1-(2-cyano-5-pyridylmethyl)-2-(nitromethylene)tetrahydropyrimidine, 1-(2-cyano-5-pyridylmethyl)-2-(nitromethylene)imidazolidine, 1-(2-trifluoromethyl-5-pyridylmethyl)-2-(nitromethylene)imidazolidine, 1-(2-trifluoromethoxy-5-pyridylmethyl)-2-(nitromethylene)tetrahydropyrimidine, 1-(2-trifluoromethoxy-5-pyridylmethyl)-2-(nitromethylene)imidazolidine, 1-(2-trifluoromethylthio-5-pyridylmethyl)-2-(nitromethylene)imidazolidine, and 1-(2-nitro-5-pyridylmethyl)-2-(nitromethylene)tetrahydropyrimidine.

The compounds of the formula (I) in accordance with this invention can be produced, for example, by the following general processes.

Process a

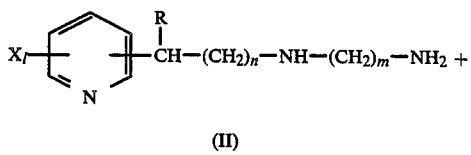

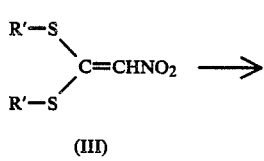

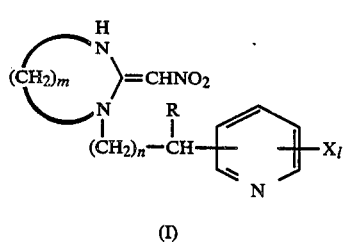

(In the formula, R, X, l, m, n and R' are the same as defined above.)

If, for example, N-(2-cyano-5-pyridylmethyl)trimethylenediamine and 1-nitro-2,2-bis(methylthio)ethylene are used as starting materials in the above process, the reaction is represented by the following scheme.

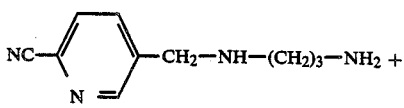

$(CH_3S)_2C=CHNO_2 \longrightarrow$

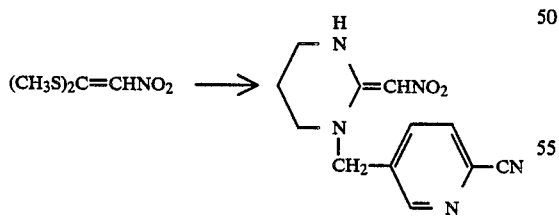

Process b

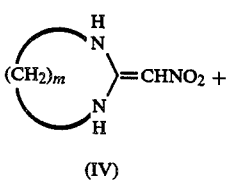

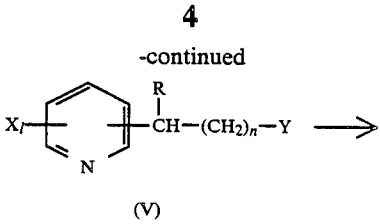

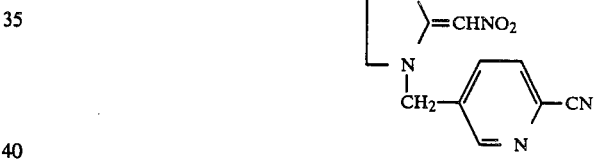

(In the formula, R, X, l, m, n and Y are as defined hereinabove.)

If 2-nitromethyleneimidazolidine and 2-cyano-5-pyridylmethyl chloride are used as starting materials in the process (b), the reaction is represented by the following reaction scheme:

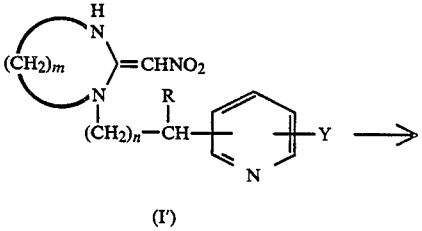

The compounds of the formula (I) in which X is a haloalkyl group, a haloalkoxy group or a haloalkylthio group and l is 1 can be produced by the following alternative process (c) in addition to the processes (a) and (b):

Process c (In the formula, R, m and n are as defined above; Y represents a halogen atom; and Z represents a haloalkyl, haloalkoxy or haloalkylthio group.)

If 1-(2-bromo-5-pyridylmethyl)-2-(nitromethylene)imidazolidine is reacted with trifluoromethyl copper in the above process, the reaction is shown by the following scheme:

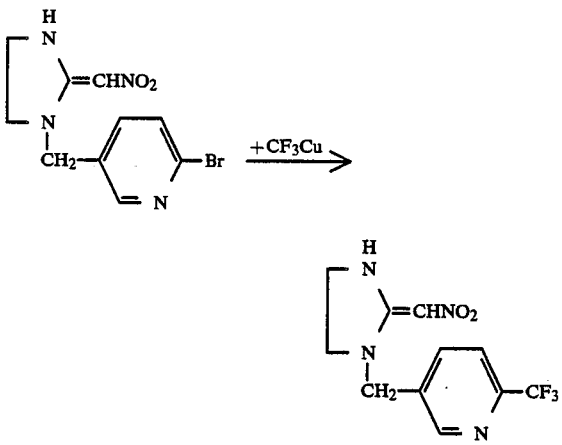

The compound of the formula (I') in process (c) is the compound described in Japanese patent applications Nos. 72,966/1984 and 132,943/1984 filed by the same applicant as the present application.

In process (c), by heating the halogen-substituted compounds of the formula (I') with trifluoromethyl copper, for example, as illustrated above, it can be converted to a trifluoromethyl substituted product (by applying the method described in Japanese Laid-Open Patent Publication No. 22,371/1979 and the method at page 989 of Pre-Prints of the 50th Spring Meeting of the Chemical Society of Japan).

The haloalkoxy or haloalkylthio-substitution product can be easily produced by reacting the halogen-substituted compound (I') with a haloalkoxide or a haloalkyl mercaptide.

In process (a), the compounds of the formula (II) as a starting material means a compound based on the aforesaid definitions of R, X, l, m and n, and preferably, R, X, l, m and n are synonymous with the preferred definitions given above.

The compounds corresponding to the formula (II) were not known before the filing date of the present application. Specific examples thereof include
N-(2-fluoromethoxy-5-pyridylmethyl)-,
N-(2-difluoromethoxy-5-pyridylmethyl)-,
N-(2-trifluoromethoxy-5-pyridylmethyl)-,
N-[1-(2-trifluoromethoxy-5-pyridyl)ethyl]-,
N-[2-(2-fluoroethoxy)-5-pyridylmethyl]-,
N-[2-(2-chloroethoxy)-5-pyridylmethyl]-,
N-[2-(2-bromoethoxy)-5-pyridylmethyl]-,
N-[2-(2,2,2-trifluoroethoxy)-5-pyridylmethyl]-,
N-[2-(1,1,2,2-tetrafluoroethoxy)-5-pyridylmethyl]-,
N-[2-(1,1,1,3,3,3-hexafluoro-2-propoxy)-5-pyridylmethyl]-,
N-(2-difluoromethylthio-5-pyridylmethyl)-,
N-(2-trifluoromethylthio-5-pyridylmethyl)-,
N-[2-(2,2,2-trifluoroethylthio)-5-pyridylmethyl]-,
N-(5-trifluoromethylthio-2-pyridylthio)-,
N-[2-(2-fluoroethylthio)-5-pyridylmethyl]-,
N-(2-nitro-5-pyridylmethyl)-,
N-(3-methoxy-2-nitro-6-pyridylmethyl)-,
N-(2-cyano-5-pyridylmethyl)-,
N-(2-thiocyanato-5-pyridylmethyl)-,
N-[1-(2-cyano-5-pyridyl)ethyl]-,
N-(2-hydroxy-5-pyridylmethyl)-,
N-(2-methoxycarbonyl-5-pyridylmethyl)-,
N-(5-methoxycarbonyl-2-pyridylmethyl)-,
N-(2-ethoxycarbonyl-5-pyridylmethyl)-,
N-[2-(2,2-dichlorovinyl)-5-pyridylmethyl]-,
N-[2-(3-fluoropropargyl)-5-pyridylmethyl]-,
N-(2-amino-5-pyridylmethyl)-,
N-(2-dimethylamino-5-pyridylmethyl)-,
N-(2-acetyl-5-pyridylmethyl)-,
N-(2-acetamido-5-pyridylmethyl)-,
N-(2-trifluoromethylsulfonyl-5-pyridylmethyl)-,
N-(2-trifluoromethylsulfinyl-5-pyridylmethyl)-,
N-(2-fluoromethyl-5-pyridylmethyl)-,
N-(2-difluoromethyl-5-pyridylmethyl)-,
N-(2-trifluoromethyl-5-pyridylmethyl)-,
N-(2-chlorodifluoromethyl-5-pyridylmethyl)-,
N-[1-(2-trifluoromethyl-5-pyridyl)ethyl]-,
N-(2-bromodifluoromethyl-5-pyridylmethyl)-,
N-(5-trifluoromethyl-2-pyridylmethyl)-,
N-[2-(2-fluoroethyl)-5-pyridylmethyl]-,
N-[2-(2-chloroethyl)-5-pyridylmethyl]-,
N-[2-(2,2,2-trifluoroethyl)-5-pyridylmethyl]-,
N-[2-(1,1,2,2-tetrafluoroethyl)-5-pyridylmethyl]-,
N-[2-(1,1,2,2,2-pentafluoroethyl)-5-pyridylmethyl]-, and
N-(3-methoxy-2-nitro-6-pyridylmethyl)-ethylenediamines and -trimethylenediamines.

The ethylenediamines and triethylenediamines of general formula (II) exemplified above can be produced by the following process.

Process a

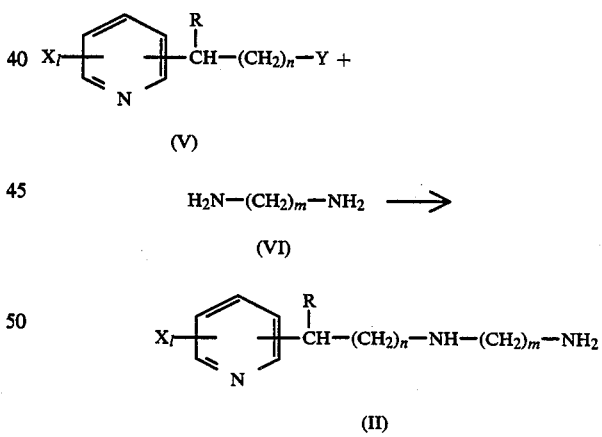

(In the formula, R, X, l, m, n and Y are as defined hereinabove.)

The compounds of the formula (V) as a starting material in process (α) are the same as the starting material in process (b) to be described in detail hereinafter.

The compounds of the formula (VI) are described in DE-OS No. 2,732,660 and French Pat. No. 1,499,785. Its specific examples are ethylenediamine and trimethylenediamine (also known as 1,3-diaminopropane).

In the practice of process (α), the desired compound of the formula (II) can be easily obtained by carrying out the reaction in an inert solvent exemplified in process (a) to be described in detail hereinafter.

The process (α) can be easily practiced by reacting an excess, for example about 5 moles, of the compound of general formula (VI) with 1 mole of the compound of general formula (V) as a reaction temperature of usually 0° to 50° C.

The compounds of the formula (II) in which n is zero can also be produced by the following alternative process:

Process β

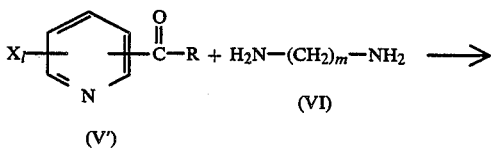

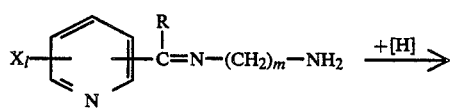

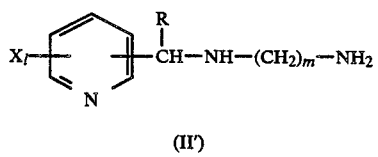

(In the formula, X, R, l and m are as defined hereinabove.)

In process (β), most of the compounds of the formula (V') are described in Japanese patent application No. 18628/1985 by the same applicant as the present application, and some of them are described in J. Med. Chem., vol. 13, pages 1124–1130. Generally, these substituted pyridinecarbaldehydes can be synthesized by the known method described in J. Org. Chem., vol. 26, pages 4912–4914, or by utilizing the reaction of reducing the corresponding pyridinecarboxylic acids or derivatives thereof to aldehydes (Org. Reaction, vol. 8, pages 218–257). As shown by the reaction scheme, according to process (β), the compounds of the formula (II') can be synthesized by reacting the pyridinecarbaldehyde or pyridylalkylketone of the formula (V') with the compounds of the formula (VI) to form an imine and reacting it with a reducing agent such as sodium borohydride (NaBH$_4$).

The compounds of the formula (II) in which R is hydrogen and n is zero can also be produced by the following alternative process:

Process γ

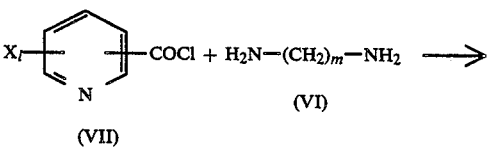

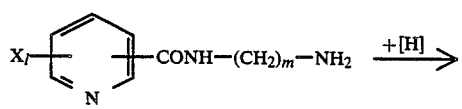

-continued
Process γ

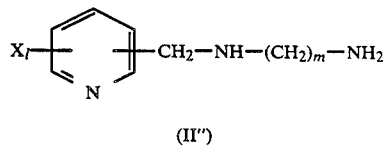

(In the formula, X, l and m are as defined above.)

As schematically shown above, the compound of the formula (II") can be synthesized by reacting the pyridylcarbonyl chloride of the formula (VII) with the compound of general formula (VI) to form a nicotinamide or picolinamide, and reacting it with a reducing agent such as lithium aluminum hydride (LIAlH$_4$).

The compounds of the formula (II) in which R is hydrogen, n is zero, and m is 3 can also be produced by the following alternative process:

Process δ

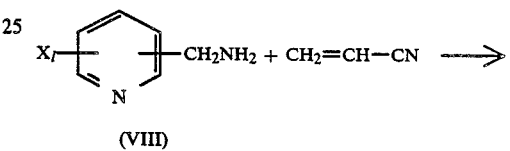

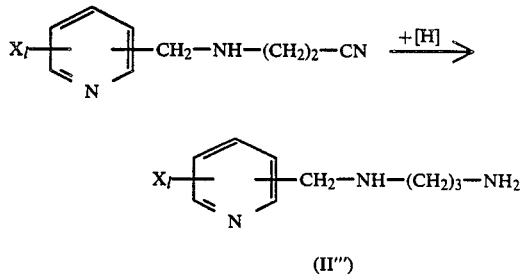

(In the formula, X and l are as defined hereinabove.)

As schematically shown above, the compounds of the formula (II''') can be synthesized by addition-reaction of acrylonitrile with the compounds of the formula (VIII) and reducing the adduct in the same way as in process (β).

The compounds of the formula (II) in which m is 2 can also be produced alternatively by the following process:

Process ε

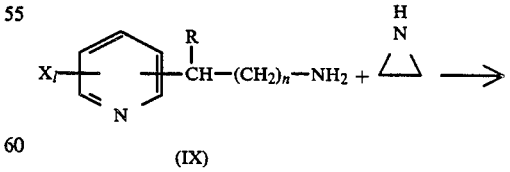

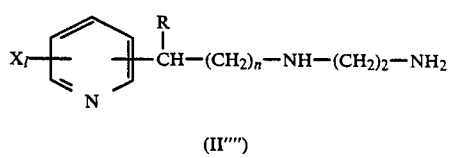

(In the formula, R, X, l and n are as defined above.)

As schematically shown above, the compounds of the formula (II'''') can be synthesized by reacting the pyridylalkylamine of the formula (IX) with ethylenimine.

The compounds of the formula (III) as a starting material in process (a) are known compounds described, for example, in Chem. Ber., vol. 100, pages 591–604. Specific examples include 1-nitro-2,2-bis(methylthio)ethylene,
1-nitro-2,2-bis(ethylthio)ethylene,
1-nitro-2,2-bis(benzylthio)ethylene, and
2-nitromethylene-1,3-dithiolane.

The compounds of the formula (IV) as a starting material in process (b) are described, for example, in Chem. Ber., vol. 100, pages 591–604. Specific examples are 2-nitromethyleneimidazolidine and 2-nitromethylenetetrahydropyrimidine.

The compounds of the formula (V) as a starting material in process (b) can be synthesized by a known method.

Specific examples of the compounds of the formula (V) include
2-fluoromethoxy-5-pyridylmethyl-,
2-difluoromethoxy-5-pyridylmethyl-,
2-trifluoromethoxy-5-pyridylmethyl-,
1-(2-trifluoromethoxy-5-pyridyl)ethyl)-,
2-(2-fluoroethoxy)-5-pyridylmethyl-,
2-(2-chloroethoxy)-5-pyridylmethyl-,
2-(2-bromoethoxy)-5-pyridylmethyl-,
2-(2,2,2-trifluoroethoxy)-5-pyridylmethyl-,
2-(1,1,2,2-tetrafluoroethoxy-5-pyridylmethyl-,
2-(1,1,1,3,3,3-hexafluoro-2-propoxy)-5-pyridylmethyl-,
2-difluoromethylthio-5-pyridylmethyl-,
2-trifluoromethylthio-5-pyridylmethyl-,
2-(2,2,2-trifluoromethylthio)-5-pyridylmethyl-,
5-trifluoromethylthio-2-pyridylthio-,
2-(2-fluoroethylthio)-5-pyridylmethyl-,
2-nitro-5-pyridylmethyl-,
3-methoxy-2-nitro-6-pyridylmethyl-,
2-cyano-5-pyridylmethyl-,
1-(2-cyano-5-pyridyl)ethyl-,
1-(2-thiocyanato-5-pyridyl)methyl-,
2-hydroxy-5-pyridylmethyl-,
2-methoxycarbonyl-5-pyridylmethyl-,
5-methoxycarbonyl-2-pyridylmethyl-,
2-ethoxycarbonyl-5-pyridylmethyl-,
2-(2,2-dichlorovinyl)-5-pyridylmethyl-,
2-(3-fluoropropargyl)-5-pyridylmethyl-,
2-amino-5-pyridylmethyl-,
2-dimethylamino-5-pyridylmethyl-,
2-acetyl-5-pyridylmethyl-,
2-acetamido-5-pyridylmethyl-,
2-trifluoromethylsulfonyl-5-pyridylmethyl-,
2-trifluoromethylsulfinyl-5-pyridylmethyl-,
2-fluoromethyl-5-pyridylmethyl-,
2-difluoromethyl-5-pyridylmethyl-,
2-trifluoromethyl-5-pyridylmethyl-,
2-chlorodifluoromethyl-5-pyridylmethyl-,
1-(2-trifluoromethyl-5-pyridyl)ethyl-,
2-bromodifluoromethyl-5-pyridylmethyl-,
5-trifluoromethyl-2-pyridylmethyl-,
2-(2-fluoroethyl)-5-pyridylmethyl-,
2-(2-chloroethyl)-5-pyridylmethyl-,
2-(2,2,2-trifluoroethyl)-5-pyridylmethyl-,
2-(1,1,2,2-tetrafluoroethyl)-5-pyridylmethyl-,
2-(1,1,2,2,2-pentafluoroethyl)-5-pyridylmethyl-, and
3-methoxy-2-nitro-6-pyridylmethylchlorides or -bromides.

The above-exemplified chlorides can be easily synthesized by a customary method of chlorinating the corresponding alcohols with, for example, thionyl chloride. The halides can also be synthesized by halogenating the side-chain methyl group with a halogenating agent such as N-bromosuccinimide or N-chlorosuccinimide.

Some trifluoromethyl- or trifluoromethoxy-substituted pyridylmethyl alcohols are described in J. Med. Chem., vol. 13, pages 1124–1130. 5-Trifluoromethyl-2-pyridylmethyl alcohol can be prepared in accordance with these synthesizing techniques by converting 2-methyl-5-trifluoromethylpyridine obtained by the reaction of 6-methylnicotinic acid with hydrofluoric acid or sulfur tetrafluoride into an N-oxide, and subjecting the N-oxide to rearrangement.

This reaction can also be applied to the synthesis of 5-methyl-2-trifluoromethylpyridine from 5-methylpicolinic acid. The novel 2-trifluoromethyl-5-pyridylmethyl bromide (or chloride) as the desired starting material can be synthesized by treating the above-mentioned 5-methyl-2-trifluoromethylpyridine with N-bromosuccinimide or N-chlorosuccinimide to mono-halogenate the methyl group at the 5-position.

2-Trifluoromethoxy-5-pyridylmethyl bromide (or chloride) can be obtained likewise by reacting 5-methyl-2-trifluoromethoxypyridine, obtained from 2-hydroxy-5-methyl-2-pyridine, with N-bromosuccinimide or N-chlorosuccinimide.

Since halogen at the ortho-position of the pyridine ring is active, a 6-haloalkoxynicotinic acid can be synthesized, for example, by reacting 6-chloronicotinic acid with an excess of a sodium alkoxide. Reduction of the product can give the starting 2-haloalkoxy-5-pyridylmethyl alcohol.

Alternatively, the haloalkyl-substituted pyridine can be directly synthesized by condensation of methylbutadiene with a haloalkanenitrile such as trifluoroacetonitrile. For example, 5-methyl-2-trifluoromethylpyridine can be obtained from methylbutadiene and trifluoroacetonitrile (by applying the methods described in J. A. C. S., vol. 78, pages 978–979; J. Org. Chem., vol. 29, pages 569–571).

With regard to the haloalkyltho-substituted pyridines, the starting pyridylmethyl chloride (or bromide) can be obtained, for example, by reacting 5-methylpyridine-2-thione (described in Synth. Commun., vol. 11, pages 273–280) with a suitable alkylating agent in the presence of an alkali to form a 2-haloalkylthio-5-methylpyridine, and treating it with N-bromosuccinimide or N-chlorosuccinimide.

Nitropyridylmethyl bromide can be synthesized from a nitropicoline and N-bromosuccinimide. For example, 2-nitro-3-pyridylmethylbromide is obtained from 3-methyl-2-nitropyridine (J. Chem. Soc., 1966, pages 315–321). By utilizing this reaction, similar pyridylmethyl halides can be synthesized. With regard to cyano-substituted pyridylalkyl halides, 2-cyano-5-hydroxymethylpyridine, for example, is obtained by the reaction of 3-hydroxymethylpyridine-N-oxide with trimethylsilyl cyanide (PCT Int. Appl. WO 8,301,446). Treatment with a halogenating agent gives pyridylmethyl halides (Gazz. Chim. Ital., vol. 105, pages 1001–1009).

In the practice of the process (a), all inert organic solvents can be used as suitable diluents.

Examples of such diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above process can be carried out over a wide temperature range, for example between about $-20°$ C. and the boiling point of the mixture, preferably between about $0°$ C. and about $100°$ C. Desirably, the reaction is carried out under normal atmospheric pressure, but it is also possible to operate under elevated or reduced pressures.

In carrying out the above process, 1 mole of the compounds of the formula (II) and 1 to about 1.2 moles, preferably 1 to about 1.1 moles of the compounds of the formula (III), for example, are reacted in an inert solvent such as an alcohol (e.g., methanol or ethanol) until the generation of mercaptan ceases. This can give the desired novel compounds of the formula (I).

Suitable diluents for the practice of the process (b) may be all of the inert organic solvents exemplified above for process (a) excepting water and alcohols. Furthermore, hydrides such as sodium hydride and potassium hydride may be cited as examples of the bases.

Process (b) can be carried out over a wide temperature range, for example at a temperature between about $0°$ C. and about $100°$ C., preferably between about $10°$ C. and about $50°$ C. The reaction is preferably carried out under atmospheric pressure, but can also be performed under elevated or reduced pressure conditions.

In the practice of the above process, the desired compounds of the formula (I) can be obtained by reacting 1 mole of the compounds of the formula (IV) with about 1 to 1.2 moles of the compounds of the formula (V) in the presence of about 1.1 to 1.2 moles of sodium hydride as a base in an inert solvent such as dimethylformamide. In process (b), it is preferred for the reaction that the compounds of the formula (IV) be converted in advance to a sodium salt by sodium hydride. Desirably, such a reaction is carried out in a nitrogen atmosphere in view of the properties of sodium hydride.

The compounds of the formula (I) in accordance with this invention also include tautomers as shown by the following formulae:

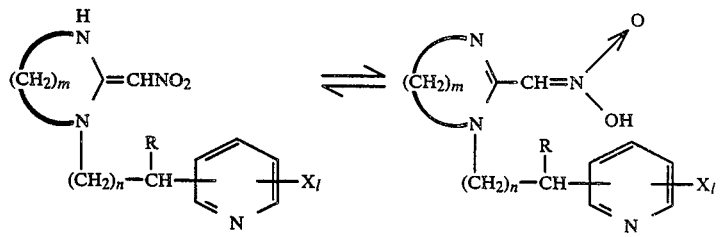

The compounds of the formula (I) in accordance with this invention can exist in the form of salts. Examples of the salts include inorganic salts, sulfonic acid salts, organic acid salts and metal salts. Accordingly, the nitromethylene derivatives of formula (I) are meant to include their salts.

The compounds of the formula (I) in accordance with this invention exhibit strong insecticidal activity, and can therefore be used as insecticides. The active compounds of this invention represented by formula (I) exhibit an accurate controlling effect against noxious insects, without causing any phytotoxicity to cultivated plants. Furthermore, the compounds of this invention can be used for the control and eradication of a wide range of pests, including sucking insects, biting insects and other plant parasites, pests on stored grains and pests causing health hazards.

Examples of the pests are shown below.
Coleopterous insects
  *Callosobruchus chinensis,*
  *Sitophilus zeamais,*
  *Tribolium castaneum,*
  *Epilachna vigitioctomaculata,*
  *Agriotes fuscicollis,*
  *Anomala rufocuprea,*
  *Leptinotarsa decemkineata,*
  *Diabrotica* spp.,
  *Monochamus alternatus,*
  *Lissorhoptrus oryzophilus,* and
  *Lyctus brunneus.*
Lepidopterous insects
  *Lymantria dispar,*
  *Malacosoma neustria,*
  *Pieris rapae,*
  *Spodoptera litura,*
  *Mamestra brassicae,*
  *Chilo suppressalis,*
  *Pyrausta nubilalis,*
  *Ephestia cautella,*
  *Adoxophyes orana,*
  *Carpocapsa pomonella,*
  *Agrotis fucosa,*
  *Galleria mellonella,*
  *Plutella maculipennis,* and
  *Phyllocnistis citrella.*
Hemipterous insects
  *Nephotettix cincticeps,*
  *Nilaparvata lugens,*
  *Pseudococcus cometocki,*
  *Unaspis yanonensis,*
  *Myzus persicae,*
  *Aphis pomi,*
  *Aphis gossypii,*

*Rhopalosiphum pseudobrassicas,*
*Stephanitis nashi,*
Nazara spp.,
*Cimex lectularius,*
*Trialeurodes vaporariorum,* and
Psylla spp.
Orthopterous insects
*Blatella germanica,*
*Periplaneta americana,*
*Gryllotalpa africana,* and
*Locusta migratoria migratoriodes.*
Isopterous insects
*Deucotermes sparatus,* and
*Coptotermes formosanus.*
Dipterous insects
*Musca domestica,*
*Aedes aegypti,*
*Hylemia platura,*
*Culex pipiens,*
*Anopheles sinensis,* and
*Culex tritaeniorhynchus.*

In the field of veterinary medicine, the novel compounds of this invention are effective against various noxious animal parasites (endo- and ecto-parasites) such as ticks, insects and worms. Examples of such animal parasites are insects such as Gastrophilus spp., Stomoxys spp., Trichodectes spp., Rhodnius spp., and *Ctenocephalides canis.*

In the present invention, substances having pesticidal activity on all these pests are sometimes called insecticides.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strangly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as hyghly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, mangnese boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The following Examples illustrate the present invention more specifically. It should be understood however that the invention is in no way limited to these examples alone.

Production Examples

EXAMPLE 1

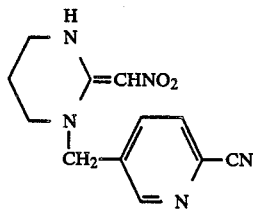
(Compound No. 1)

A mixture of N-(2-cyano-5-pyridylmethyl)trimethylenediamine (1.9 g), 1-nitro-2,2-bis(methylthio)ethylene (1.6 g) and ethanol (30 ml) was refluxed for 5 hours with stirring. The reaction mixture was cooled to room temperature. The precipitated crystals were collected by filtration, and washed with ethanol to give pale yellow 1-(2-cyano-5-pyridylmethyl)-2-(nitromethylene)-tetrahydropyrimidine (1.6 g). mp. 214°–216° C.

EXAMPLE 2

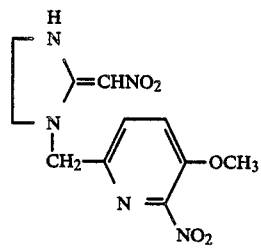
(Compound No. 2)

Nitromethyleneimidazolidine (1.3 g) was dissolved in dry dimethylformamide (15 ml), and sodium hydride (0.26 g) was added. The mixture was stirred at room temperature until the generation of hydrogen ceased. Subsequently, a solution of 2.4 g of 3-methoxy-2-nitro-6-pyridylmethyl bromide in 5 ml of dimethylformamide was added, and the mixture was stirred at 60° C. for 15 minutes. The reaction mixture was cooled to room temperature, poured into 50 ml of ice water, and extracted with dichloromethane. Dichloromethane was distilled off under reduced pressure, and ethanol was added to the residue to precipitate crystals. The crystals were collected by filtration and washed with ethanol to give 1-(3-methoxy-2-nitro-6-methylpyridylmethyl)-2-nitromethyleneimidazolidine (0.4 g). mp. 177°–181° C.

EXAMPLE 3

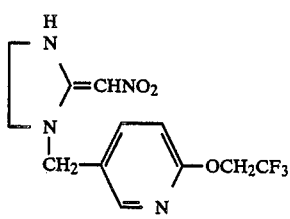
(Compound No. 11)

2,2,2-Trifluoroethanol (3.6 g) was dissolved in toluene (20 ml), and sodium hydride (0.7 g) was added to prepare a sodium salt of 2,2,2-trifluoroethanol. Then, 3 g of 1-(2-bromo-5-pyridylmethyl)-2-(nitromethylene)imidazolidine (the known compound described in Japanese patent application No. 132,943/1984) was added, and the mixture was heated at 80° C. for 8 hours. Toluene was distilled off under reduced pressure, and the residue was poured into 20 ml of ice water and then neutralized. The aqueous solution was extracted with dichloromethane, and the extract was purified by silica gel column chromatography to give 1-[2-(2,2,2-trifluoroethoxy)-5-pyridylmethyl]-2-(nitromethylene)-imidazolidine. mp. 132°–135° C.

Table 1 below shows examples of compounds of general formula (I) in accordance with this invention which can be prepared by the method of Example 1, 2 or 3.

TABLE 1

| Compound No. | m | n | R | Bonding portion on the pyridine ring | $X_l$ | |
|---|---|---|---|---|---|---|
| 3 | 2 | 0 | H | 5- | 2-OCH$_2$F | |
| 4 | 2 | 0 | H | 5- | 2-OCHF$_2$ | |
| 5 | 2 | 0 | H | 5- | 2-OCF$_3$ | |
| 6 | 3 | 0 | H | 5- | 2-OCF$_3$ | |
| 7 | 2 | 0 | —CH$_3$ | 5- | 2-OCF$_3$ | |
| 8 | 3 | 0 | H | 5- | 2-OCH$_2$CH$_2$F | |
| 9 | 2 | 0 | H | 5- | 2-OCH$_2$CH$_2$Cl | |
| 10 | 2 | 0 | H | 5- | 2-OCH$_2$CH$_2$Br | |
| 12 | 3 | 0 | H | 5- | 2-OCH$_2$CF$_3$ | |
| 13 | 2 | 0 | H | 5- | 2-OCF$_2$CHF$_2$ | |
| 14 | 2 | 0 | H | 5- | 2-OCH(CF$_3$)$_2$ | |
| 15 | 3 | 0 | H | 5- | 2-SCF$_3$ | |
| 16 | 2 | 0 | H | 5- | 2-SCF$_3$ | |
| 17 | 2 | 1 | H | 5- | 2-SCH$_2$CF$_3$ | |
| 18 | 2 | 0 | H | 2- | 5-SCF$_3$ | |
| 19 | 2 | 0 | H | 5- | 2-SCH$_2$CH$_2$F | |
| 20 | 2 | 0 | H | 5- | 2-NO$_2$ | |
| 21 | 2 | 0 | H | 5- | 2-CN | mp. 155–158° C. |
| 22 | 2 | 0 | —CH$_3$ | 5- | 2-CN | |
| 23 | 2 | 0 | H | 5- | 2-OH | |
| 24 | 3 | 0 | H | 5- | 2-C(O)—OCH$_3$ | |
| 25 | 2 | 0 | H | 2- | 5-C(O)—OCH$_3$ | |
| 26 | 2 | 0 | H | 5- | 2-C(O)—OC$_2$H$_5$ | |
| 27 | 2 | 0 | H | 5- | 2-CH=C(CF$_3$)$_2$ | |
| 28 | 3 | 0 | H | 5- | 2-CH=CCl$_2$ | |
| 29 | 2 | 0 | H | 5- | 2-CH$_2$≡CF | |
| 30 | 2 | 0 | H | 5- | 2-CH$_2$F | |
| 31 | 2 | 0 | H | 5- | 2-CHF$_2$ | |
| 32 | 3 | 0 | H | 5- | 2-CHF$_2$ | |
| 33 | 2 | 0 | H | 5- | 2-CF$_3$ | mp. 158–159° C. |
| 34 | 3 | 0 | H | 5- | 2-CF$_3$ | |
| 35 | 2 | 0 | —CH$_3$ | 5- | 2-CF$_3$ | |
| 36 | 2 | 0 | H | 2- | 5-CF$_3$ | |
| 37 | 2 | 0 | H | 5- | 2-CH$_2$CH$_2$F | |
| 38 | 2 | 0 | H | 5- | 2-CH$_2$CH$_2$Cl | |
| 39 | 2 | 0 | H | 5- | 2-CH$_2$CF$_3$ | |

TABLE 1-continued

| Compound No. | m | n | R | Bonding portion on the pyridine ring | $X_l$ |
|---|---|---|---|---|---|
| 40 | 2 | 0 | H | 5- | 2-CF$_2$CHF$_2$ |
| 41 | 2 | 0 | H | 5- | 2-CF$_2$CF$_3$ |
| 42 | 2 | 1 | H | 5- | 2-CF$_3$ |
| 43 | 2 | 0 | H | 5- | 2-NH$_2$ |
| 44 | 2 | 0 | H | 5- | 2-C(=O)—CH$_3$ |
| 45 | 2 | 0 | H | 5- | 2-N(CH$_3$)$_2$ |
| 46 | 2 | 0 | H | 5- | 2-NHCCH$_3$ (=O) |
| 47 | 3 | 0 | H | 2- | 5-CF$_3$ |
| 48 | 2 | 0 | H | 5- | 2-CClF$_2$ |
| 49 | 2 | 0 | H | 5- | 2-CBrF$_2$ |
| 50 | 2 | 0 | H | 5- | 2-SCN |

EXAMPLE 4

(Compound No. II-21)

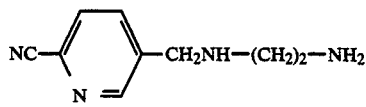

A solution of 2-cyano-5-pyridylmethyl chloride (4.6 g) in acetonitrile (20 ml) was added dropwise at 5° to 10° C. to a solution of ethylenediamine (9 g) in acetonitrile (50 ml). After the addition, the mixture was stirred at room temperature for 3 hours. Acetonitrile and the excess of ethylenediamine were distilled off under reduced pressure from the mixture. Dichloromethane was added to the residue, and a portion soluble in dichloromethane was recovered. Dichloromethane was distilled off under reduced pressure, and volatile materials were removed at 50° C. and 1 mmHg to give N-(2-cyano-5-pyridylmethyl)ethylenediamine (4.5 g) as a colorless oil. $n_D^{20}$:1.5718

EXAMPLE 5

(Compound No. 47)

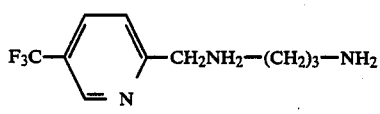

5-Trifluoromethylpicolinealdehyde (3.5 g) was added dropwise at room temperature to a solution of trimethylenediamine (7.4 g) in benzene (70 ml). After the addition, the mixture was gradually heated with stirring, and then refluxed for 2 hours while removing water that azeotroped. Benzene was distilled off under reduced pressure. The residue was dissolved in ethanol (100 ml), and sodium borohydride (0.9 g) was added little by little while the solution was stirred at 10° to 15° C. The mixture was then stirred at room temperature for 2 hours, and ethanol was distilled off at less than 30° C. Dichloromethane was added to the residue, and a portion soluble in dichloromethane was separated. Dichloromethane was distilled off under reduced pressure, and volatile materials were removed at 1 mmHg and less than 60° C. to give N-(5-trifluoromethyl-2-pyridylmethyl)trimethylenediamine (3.5 g) as a colorless oil. $n_D^{20}$:1.4651.

Table 2 specifically shows compounds of the formula (II) which can be prepared by the same method as in Example 4 or 5.

TABLE 2

$X_l$—[pyridyl]—CH(R)—(CH$_2$)$_n$NH—(CH$_2$)$_m$—NH$_2$

| Compound No. | m | n | R | Bonding portion on the pyridine ring | $X_l$ |
|---|---|---|---|---|---|
| II-1 | 3 | 0 | H | 5- | 2-CN |
| II-2 | 2 | 0 | H | 6- | 2-NO$_2$, 3-OCH$_3$ |
| II-3 | 2 | 0 | H | 5- | 2-OCH$_2$F |
| II-4 | 2 | 0 | H | 5- | 2-OCHF$_2$ |
| II-5 | 2 | 0 | H | 5- | 2-OCF$_3$ |
| II-6 | 3 | 0 | H | 5- | 2-OCF$_3$ |
| II-7 | 2 | 0 | —CH$_3$ | 5- | 2-OCF$_3$ |
| II-8 | 3 | 0 | H | 5- | 2-OCH$_2$CH$_2$F |
| II-9 | 2 | 0 | H | 5- | 2-OCH$_2$CH$_2$Cl |
| II-10 | 2 | 0 | H | 5- | 2-OCH$_2$CH$_2$Br |
| II-12 | 3 | 0 | H | 5- | 2-OCH$_2$CF$_3$ |
| II-13 | 2 | 0 | H | 5- | 2-OCF$_2$CHF$_2$ |
| II-14 | 2 | 0 | H | 5- | 2-OCH(CF$_3$)$_2$ |
| II-15 | 3 | 0 | H | 5- | 2-SCF$_3$ |
| II-16 | 2 | 0 | H | 5- | 2-SCF$_3$ |
| II-17 | 2 | 1 | H | 5- | 2-SCH$_2$CF$_3$ |
| II-18 | 2 | 0 | H | 2- | 5-SCF$_3$ |
| II-19 | 2 | 0 | H | 5- | 2-SCH$_2$CH$_2$F |
| II-20 | 2 | 0 | H | 5- | 2-NO$_2$ |
| II-22 | 2 | 0 | —CH$_3$ | 5- | 2-CN |
| II-23 | 2 | 0 | H | 5- | 2-OH |
| II-24 | 3 | 0 | H | 5- | 2-C(=O)—OCH$_3$ |
| II-25 | 2 | 0 | H | 2- | 5-C(=O)—OCH$_3$ |
| II-26 | 2 | 0 | H | 5- | 2-C(=O)—OC$_2$H$_5$ |
| II-27 | 2 | 0 | H | 5- | 2-CH=C(CF$_3$)$_2$ |
| II-28 | 3 | 0 | H | 5- | 2-CH=CCl$_2$ |
| II-29 | 2 | 0 | H | 5- | 2-CH$_2$C≡CF |
| II-30 | 2 | 0 | H | 5- | 2-CH$_2$F |
| II-31 | 2 | 0 | H | 5- | 2-CHF$_2$ |
| II-32 | 3 | 0 | H | 5- | 2-CHF$_2$ |
| II-33 | 2 | 0 | H | 5- | 2-CF$_2$ $n_D^{20}$ 1.4811 |
| II-34 | 3 | 0 | H | 5- | 2-CF$_3$ |
| II-35 | 2 | 0 | —CH$_3$ | 5- | 2-CF$_3$ |
| II-36 | 2 | 0 | H | 2- | 5-CF$_3$ |
| II-37 | 2 | 0 | H | 5- | 2-CH$_2$CH$_2$F |
| II-38 | 2 | 0 | H | 5- | 2-CH$_2$CH$_2$Cl |
| II-39 | 2 | 0 | H | 5- | 2-CH$_2$CF$_3$ |
| II-40 | 2 | 0 | H | 5- | 2-CF$_2$CHF$_2$ |
| II-41 | 2 | 0 | H | 5- | 2-CF$_2$CF$_3$ |
| II-42 | 2 | 1 | H | 5- | 2-CF$_3$ |

TABLE 2-continued

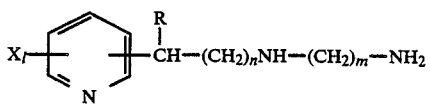

| Compound No. | m | n | R | Bonding portion on the pyridine ring | $X_l$ |
|---|---|---|---|---|---|
| II-43 | 2 | 0 | H | 5- | 2-$NH_2$ |
| II-44 | 2 | 0 | H | 5- | 2-C(=O)-$CH_3$ |
| II-45 | 2 | 0 | H | 5- | 2-$N(CH_3)_2$ |
| II-46 | 2 | 0 | H | 5- | 2-NHC(=O)$CH_3$ |
| II-48 | 2 | 0 | H | 5- | 2-$CClF_2$ |
| II-49 | 2 | 0 | H | 5- | 2-$CBrF_2$ |
| II-50 | 2 | 0 | H | 5- | 2-SCN |

EXAMPLE 6

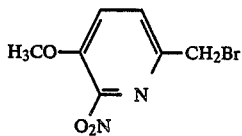

A catalytic amount of α,α'-azobis(isobutyronitrile) was added to 3-methoxy-6-methyl-2-nitropyridine (described in Acta Chem. Scand., vol. 23, pages 1791–1796) (7.1 g), N-bromosuccinimide (7.1 g) and carbon tetrachloride (80 ml), and the mixture was refluxed for 16 hours. After the reaction, while the reaction mixture was still hot, it was suction-filtered to separate the insoluble succinimide. The filtrate was cooled to room temperature whereupon the unreacted 3-methoxy-6-methyl-2-nitropyridine precipitated as crystals. The crystals were separated by filtration. The residue was concentrated and then vacuum distilled to give 3-methoxy-2-nitro-6-pyridylmethyl bromide (2.1 g).

bp. 128°–131° C./0.6 mmHg

EXAMPLE 7

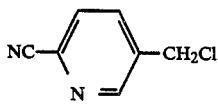

2-Cyano-5-hydroxymethylpyridine (13.4 g) and pyridine (8.7 g) were dissolved in toluene (150 ml), and a solution of p-toluenesufonyl chloride (19.1 g) in toluene (50 ml) was added dropwise at room temperature to the solution. After the addition, the mixture was gradually heated, and stirred at 70° to 80° C. for 4 hours. The reaction mixture was cooled to room temperature, and washed with water. The organic layer was dried. Toluene was distilled off under reduced pressure. The residue was purified by silica gel column chromatography to give 2-cyano-5-pyridylmethyl chloride (7.7 g) as colorless crystals.

mp. 45°–47° C.

EXAMPLE 8

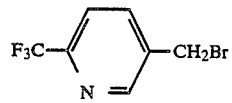

5-Methyl-2-trifluoromethylpyridine (see J. Org. Chem., vol. 29, pages 569–571) (8.1 g) was dissolved in 50 ml of carbon tetrachloride, and N-bromosuccinimide (8.9 g) and a catalytic amount of benzoyl peroxide were added. The mixture was refluxed for 7 hours with stirring. The reaction mixture was cooled, and insoluble materials were collected by filtration. The filtrate was concentrated under reduced pressure, and the residue was purified by silica gel column chromatography to give 2-trifluoromethyl-5-pyridylmethyl bromide (also known as 5-bromomethyl-2-trifluoromethylpyridine) (7.3 g).

mp. 36°–37° C.

Biological tests

Comparative Compound A-1:

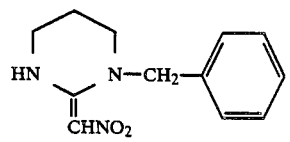

the compound described in DE-OS No. 2,514,402. This compound was used as comparison compound in the following Examples 9, 10, 11.

EXAMPLE 9 (biological test)

Test on *Nephotettix cincticeps* having resistance to organophosphorus agents:

Preparation of a test chemical

Solvent: 3 parts by weight of xylene

Emulsifier: 1 part by weight of polyoxyethylene alkyl phenyl ether

To form a suitable preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the kill ratio was calculated.

In this test, for example, the following compounds from the preparation examples show a superior action compared to the prior art: Compounds No. 1 and 11.

EXAMPLE 10 (biological test)

Test on planthoppers:
Testing method

A water dilution in a predetermined concentration of the active compound prepared as in Example 8 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stael of a strain which showed resistance to organophosphorus chemicals were released into the net. The pots were left to stand in a constant temperature chamber and the number of dead insects was examined two days later. The kill ratio was then calculated.

In the same way as above, the kill ratio was calculated on *Sogatella furcifera* Horvath and organophosphorus-resistant *Laodelphax striatellus* Fallen.

In this test, for example, the following compounds from the preparation examples show a superior action compared to the prior art: Compounds No. 1, 11, 12, 21 and 33.

EXAMPLE 11 (biological test)

Test on *Myzus persicae* (green peach aphids) having resistance to organophosphorus chemicals and carbamate chemicals:
Testing method Green peach aphids which had been bred and had resistance to organophosphorus chemicals and carbamate chemicals were inoculated on eggplant seedlings (black elongate eggplants), about 20 cm tall, grown in unglazed pots having a diameter of 15 cm (about 200 aphids per seedling). One day after the inoculation, a water dilution of each active compound at a predetermined concentration in Example 8 was sprayed in a sufficient amount onto the plants using a spray gun. After the spraying, the pots were left to stand in a greenhouse at 28° C. Twenty-four hours after the spraying, the kill ratio was calculated. For each compound, the test was carried out through two replicates.

In this test, for example, the following compounds from the preparation examples show a superior action compared to the prior art: Compounds No. 11, 12 and 13.

Examples 9, 10 and 11 show typical examples of insecticidal uses, and the compounds of this invention shown herein are also typical examples. It should be understood that the invention is not to be limited to these examples alone.

It will be understood that the specification and examples are illustrative but not limitative of the present invention and that other embodiments within the spirit and scope of the invention will suggest themselves to those skilled in the art.

We claim:

1. A nitromethylene derivative of the formula

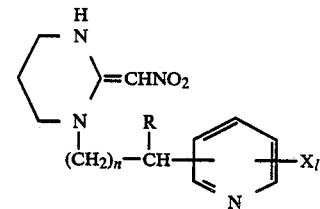

wherein
R is a hydrogen atom or an alkyl group having 1 to 4 carbon atoms,
X is a halo-$C_1$-$C_4$ alkyl group, a halo-$C_1$-$C_4$ alkoxy group, a halo-$C_1$-$C_4$ alkylthio group, a halo-$C_1$-$C_4$ alkylsulfinyl group, a halo-$C_1$-$C_4$ alkylsulfonyl group, a nitro group, a cyano group, a thiocyanato group, a halo-$C_2$-$C_3$ alkenyl group, a halo-$C_2$-$C_3$ alkynyl group, a hydroxyl group, a $C_1$-$C_2$ alkoxycarbonyl group, an amino group, an acetyl group, a di-$C_1$-$C_2$ alkylamino group, an acetamide group or a methoxy group,
$l$ is 1 or 2 provided that, when $l$ is 1 X does not represent a methoxy group, and when $l$ is 2 at least one X is not a methoxy group, and
n is 0 or 1.

2. A compound according to claim 1, wherein
X is a $C_1$-$C_2$ fluoro-substituted alkyl group, a $C_1$-$C_2$ fluoro-substituted alkoxy group, a $C_1$-$C_2$ fluoro-substituted alkylthio group, a $C_1$-$C_2$ fluoro-substituted alkylsulfinyl group, a $C_1$-$C_2$ fluoro-substituted alkylsulfonyl group, a nitro group, a cyano group, a thiocyanato group, a chloro-substituted vinyl group, a fluoro-substituted propargyl group, a hydroxy group, a methoxy-carbonyl group, an amino group, an acetyl group, a dimethylamino group or an acetamide group and
n is 0.

3. A compound according to claim 1 wherein R is a hydrogen atom or a methylgroup, and X is a $C_1$-$C_2$ fluoro-substituted alkyl group, a $C_1$-$C_2$ fluoro-substituted alkoxy group, a $C_1$-$C_2$ fluoro-substituted alkylthio group, a $C_1$-$C_2$ fluoro-substituted alkylsulfinyl group, a $C_1$-$C_2$ fluoro-substituted alkylsulfonyl group, a nitro grouip, a cyano group, a thiocyanato group, a chloro-substituted vinyl group, a fluoro-substituted propargyl group, a hydroxy group, a methoxy-carbonyl group, an amino group, an acetyl group, a dimethylamino group or an acetamide group.

4. A compound according to claim 1 wherein such compound is 1-(2-cyano-5-pyridylmethyl)-2-nitromethylene tetrahydropyrimidine of the formula

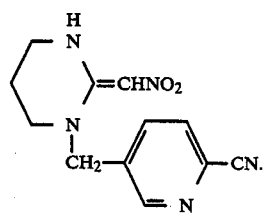

5. A compound according to claim 1 wherein such compound is 1-[2-(2,2,2-trifluoroethoxy)-5-pyridylmethyl]-2-nitromethylene-tetrahydropyrimidine of the formula

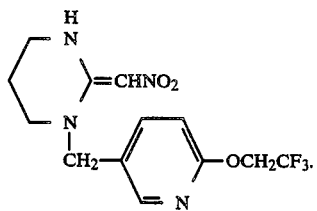

6. An insecticidal composition comprising an insecticidally effective amount of a compound according to claim 1 in admixture with a diluent.

7. A method of combating insects which comprises applying to such insects or to an insect habitat an insecticidally effective amount of a compound according to claim 1.

8. The method according to claim 7 wherein such compound is 1-(2-cyano-5-pyridylmethyl)-2-nitromethylene tetrahydropyrimidine, or 1-[2-(2,2-trifluoroethyoxy)-5-pyridylmethyl]-2-nitromethylene-tetrahydropyrimidine.

* * * * *